(12) United States Patent
Lee et al.

(10) Patent No.: US 7,838,049 B2
(45) Date of Patent: Nov. 23, 2010

(54) EXTRACTS AND COMPOUNDS FOR INHIBITING TYROSINASE ACTIVITY

(75) Inventors: Mei-Hsien Lee, Taipei (TW); Feng-Lin Hsu, Taipei (TW); Yan-Ling Liu, Taipei (TW)

(73) Assignee: Taipei Medical University, Taipei (TW)

( * ) Notice: Subject to any disclaimer, the term of this patent is extended or adjusted under 35 U.S.C. 154(b) by 0 days.

(21) Appl. No.: 12/358,422

(22) Filed: Jan. 23, 2009

(65) Prior Publication Data

US 2010/0189826 A1    Jul. 29, 2010

(51) Int. Cl.
*A61K 36/00* (2006.01)

(52) U.S. Cl. ..................................................... 424/725

(58) Field of Classification Search ....................... None
See application file for complete search history.

(56) References Cited

OTHER PUBLICATIONS

B. J. Abbott et al.: Screening Data From the Cancer Chemotherapy National Service Center Screening Laboratories, XXXVII. Plant Extracts; Cancer Research, 1966, vol. 26, 1302-1453.
Yi Dai et al.: "Biphenyl Glycosides from the Fruit of Pyracantha fortuneana," J. Nat. Prod. 2006, 69, 1022-1024.

*Primary Examiner*—Susan C Hoffman
(74) *Attorney, Agent, or Firm*—McDonnell Boehnen Hulbert & Berghoff LLP

(57) ABSTRACT

The invention provides a *Pyracantha koidzumii* extract and new compounds isolated from the extract and their derivatives. This extract and these compounds have activity in inhibiting tyrosinase.

15 Claims, 4 Drawing Sheets

EXTRACTS AND COMPOUNDS FOR INHIBITING TYROSINASE ACTIVITY

FIELD OF THE INVENTION

The invention relates to a *Pyracantha koidzumii* extract and new compounds isolated from the extract and their derivatives. This extract and these compounds have activity in inhibiting tyrosinase. In particular, the invention relates to the ethyl acetate extract of *Pyracantha koidzumii*.

BACKGROUND OF THE INVENTION

Melanin is the black pigment in hair and skin and is synthesized from amino acid tyrosine by melanosomes. Melanosomes are organelles found in melanocytes, a cell type present at the dermis-epidermis junction. Melanin plays an important role in protecting human body from the harmful effects of ultraviolet rays. Melanin is also important in medical science and cosmetology. The biosynthesis pathway of melanin involves the catalytic hydroxylation of tyrosine to L-3,4-dihydroxyphenylalanine (L-DOPA) by tyrosinase and the conversion of L-DOPA to dopachrome. Tyrosinase (EC 1.14.18.1) is a copper-containing monooxygenase that is widely distributed in nature. Its primary metabolic function is to catalyze the oxidative degradation of the amino acid tyrosine. This degradation takes slightly different routes in animals, plants and microbes, but the rate-controlling first steps—those catalyzed by tyrosinase—are the same in virtually all living species. In animals, including humans, tyrosinase first transforms tyrosine into 3,4-dihydroxyphenylalanine (DOPA), then to the corresponding quinone (DOPAquinone), and finally to 2-carboxy-2,3-dihydroindole-5,6-quinone (DOPAchrome), which is further converted by other enzymes to still more highly oxidized materials including the melanin substances responsible for skin pigmentation.

Excessive formation of melanin following prolonged sun exposure or due to disorders of epidermal melanin units is responsible for erythema, sunburn, melasma, ephelides, and pigmented cosmetic dermatitis. There have been several reports on use of inhibitors of tyrosinase such as hydroquinone and its derivatives, kojic acid, catechols, mercaptoamines, alpha hydroxy acids, etc., in cosmetic or pharmaceutical compositions to regulate skin pigmentation. Taketsugu Tadokoro indicates that tyrosinase is the most critical enzyme for synthesis of pigment, and its levels showed a marked response to UV (J Invest Dermatol 124:1326-1332, 2005). The correlation between melanoma and tyrosinase inhibition is accepted by the medical profession. Thus, development of agents capable of modulating the enzyme activity of tyrosinase will have considerable value in the control of the above-mentioned undesirable skin conditions (Hideya Ando et al., Journal of Investigative Dermatology (2007) 127, 751-761). The pharmaceutical, cosmetic, and food industries and the like all feel the need to develop agents for tyrosinase inhibition and for prevention and therapy of symptoms resulting from undesirable effects of tyrosinase activity.

Non-toxic natural products useful in the formulation of cosmetics and pharmaceuticals are of considerable interest. Firethorn (*Pyracantha*) is a genus of large thorny evergreen shrubs in the family Rosaceae, subfamily Maloideae. It is native to the area from southeast Europe to southeast Asia and closely related to Cotoneaster, but has serrated leaf margins and numerous thorns (Cotoneaster is thornless). A. Falodun et al. indicates that the presence of active principles in the leaf extracts of *P. staudtii* may be responsible for some of the remedies in traditional medicines for threatened abortion and dysmenorrheal (Pak J Pharm Sci. 2005 October; 18 (4):31-5). Otsuka H et al. discloses that *Pyracantha crenulata* roem has an anti-inflammatory effect (Chem Pharm Bull (Tokyo). 1981 November; 29(11):3099-104). CN 1765912 discloses an extract of *Pyracantha fortuneana* with water, methanol, ethanol, propanol, butanol, acetone or their mixtures which can remove oxygen free radicals. WO 0135971 discloses whitening compositions for oral administration which contain a solvent extract of a plant belonging to Rosaceae *Pyracantha* and utilization of the same, wherein the water extract and water/ethanol extract of *Pyracantha fortuneana* are effective in inhibiting tyrosinase. Japanese Publication No. 05-058870 provides an extract of Rosaceae *Pyracantha* with water, methanol, ethanol, propanol or their mixture which has beautifying and whitening effects. Furthermore, Jiang et al. finds that an extract of *Pyracantha koidzumii* has less cytotoxic and higher cellular tyrosinase inhibitory activity. Other studies indicate that *Pyracantha koidzumii* is effective in inhibiting tumors (Cancer Res. 1966; 26B(11):1302-453) and *Pyracantha fortuneana* has effects on blood coagulation (Zhong Yao Cai 2001; 24(12):874-6). The ingredients of *Pyracantha* including carotenoid, flavonoid, glycoside and sterol derivatives have been isolated from *Pyracantha*. In particular, Dai Y et al. finds tyrosinase-inhibiting biphenyl glycosides such as 3,3'-dihydroxy-5'-methoxy-(1,1'-biphenyl)-4-O-beta-d-glucoside, 4'-hydroxy-2,3',5'-trimethoxy-(1,1'-biphenyl)-2'-O-beta-d-glucoside, 4'-hydroxy-3',5'-dimethoxy-(1,1'-biphenyl)-2-O-beta-d-glucoside, 2,4'-dihydroxy-3',5'-dimethoxy-(1,1'-biphenyl)-3-O-beta-d-glucoside, and 3,4'-dihydroxy-3',5'-dimethoxy-(1,1'-biphenyl)-4-O-beta-d-glucoside (J. Nat. Prod. 2006; 69(7):1022-1024).

However, none of the *Pyracantha koidzumii* extracts provided by the above-mentioned prior art references shows superior tyrosinase inhibitory activity. There is still a need for tyrosinase inhibitors capable of effectively inhibiting the activity of tyrosine and which can be used on a long-term basis without undesirable side effects on the human skin.

SUMMARY OF THE INVENTION

The invention provides a *Pyracantha koidzumii* extract which is produced by extracting *Pyracantha koidzumii* with ethanol to obtain an ethanol extract and extracting the ethanol extract with ethyl acetate.

The invention also provides new compounds isolated from the *Pyracantha koidzumii* extract and their derivatives.

The invention further provides a method of preparing a *Pyracantha koidzumii* extract which comprises the following steps: extracting *Pyracantha koidzumii* with ethanol to obtain an ethanol extract and extracting the ethanol extract with ethyl acetate to obtain the said extract.

DETAILED DESCRIPTION OF THE INVENTION

Figure 1:
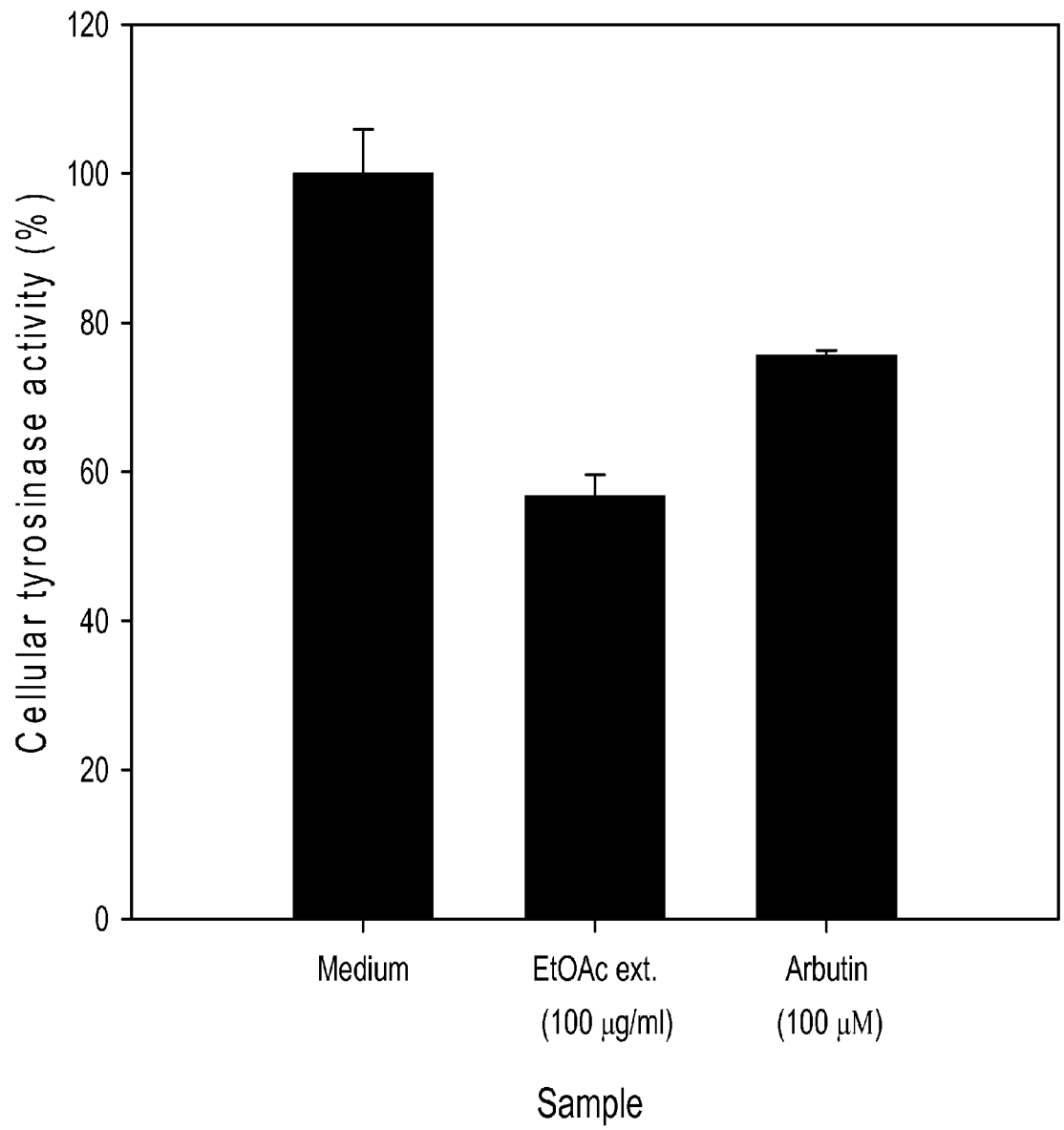
FIG. 1 shows the expression of cellular tyrosinase inhibitory activities treated by EtOAc extract in HEMn.

The invention discovers that the ethyl acetate fraction of ethanol extract of *Pyracantha koidzumii* and two new compounds in the fraction have tyrosinase inhibitory activity. By inhibiting tyrosinase, the fraction and the compounds stated herein are effective in whitening skin and can be used in prevention and therapy of symptoms resulting from undesirable effects of tyrosinase activity.

The invention provides a *Pyracantha koidzumii* extract which is produced by extracting *Pyracantha koidzumii* with ethanol to obtain an ethanol extract and then extracting the ethanol extract with ethyl acetate.

According to the invention, plants of *Pyracantha koidzumii* (preferably its fruit) are pressed and extracted with ethanol to obtain the raw extract. The raw extract is further extracted with ethyl acetate. Any extraction technique known in this art may be employed to prepare the extract according to the invention. The resulting ethyl acetate extract can be further fractioned by liquid phase chromatography using solvent elution. Preferably, the liquid chromatography is high performance liquid chromatography (HPLC) or reverse-phase HPLC and the solvent is methanol or ethanol. According to the invention, the ethyl acetate extract can be further fractioned with HPLC with $C_8$ to $C_{18}$ column by a gradient elution of water to methanol, and optionally, a gradient elution of methanol. According to one embodiment of the invention, 10% to 100% methanol (preferably about 20% to 50%) is used in the gradient elution of methanol. More preferably, about 20%, 22%, or 50% methanol is used. According to one embodiment of the invention, *Pyracantha koidzumii* is extracted with ethanol to obtain an ethanol extract and the resulting ethanol extract is extracted with ethyl acetate. Subsequently, the resulting ethyl acetate extract is fractioned by HPLC with gradient elution of 100% water to 100% methanol to obtain seven fractions, of which the third fraction is collected and further fractioned. The said third fraction is fractioned by HPLC with gradient elution of 100% water to 100% methanol to obtain eight fractions, of which the fifth fraction is collected and further fractioned. The said fifth fraction is fractioned by HPLC with about 22% methanol to obtain a new compound, 3,4-dihydroxy-5-methoxybiphenyl-2'-O-β-D-glucopyranoside (MHL-1). According to another embodiment of the invention, *Pyracantha koidzumii* is extracted with ethanol to obtain an ethanol extract and the resulting ethanol extract is extracted with ethyl acetate. Subsequently, the resulting ethyl acetate extract is fractioned by HPLC with gradient elution of 100% water to 100% methanol to obtain seven fractions, of which the fifth fraction is collected and further fractioned. The said fifth fraction is fractioned by HPLC with gradient elution of 100% water to 100% methanol to obtain ten fractions, of which the fourth fraction is collected and further fractioned. The said fourth fraction is fractioned by HPLC with 100% water to 100% methanol to obtain eight fractions, of which the second fraction is collected and further fractioned. The second fraction is fractioned by HPLC gradient elution of 100% water to 100% methanol to obtain seven fractions, of which the first fraction is collected and further fractioned. The first fraction is fractioned with about 50% methanol to obtain a new compound, 3,6-dihydroxy-2,4-dimethoxy-dibenzofuran (MHL-2).

According to the invention, two new compounds are isolated and purified from the *Pyracantha koidzumii* extract. These two compounds are 3,4-dihydroxy-5-methoxybiphenyl-2'-O-β-D-glucopyranoside (MHL-1) and 3,6-dihydroxy-2,4-dimethoxy-dibenzofuran (MHL-2).

3,4-dihydroxy-5-methoxybiphenyl-2'-O-β-D-glucopyranoside

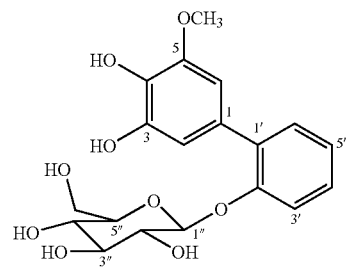

3,6-dihydroxy-2,4-dimethoxy-dibenzofuran

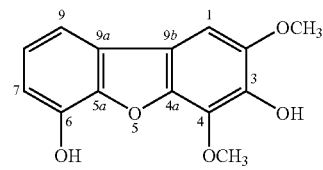

According to the invention, the compounds isolated from the *Pyracantha koidzumii* extract are further modified to obtain the compounds having the following general formulae:

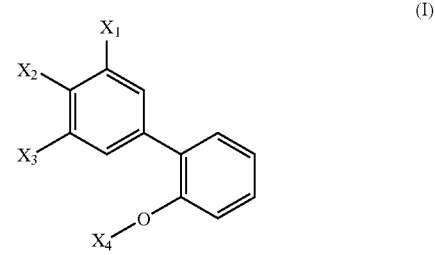

(I)

wherein $X_1$ and $X_3$ are independently OH, O-lower alkyl, $NH_2$, NH-lower alkyl, SH or S-lower alkyl;

$X_2$ is OH; and $X_4$ is glucopyranose, galactopyranose, mannopyranose, ribopyranose, arabinopyranose, xylopyranose, fructofuranose, ribofuranose, arabinofuranose or xylofuranose;

and pharmaceutically or cosmetically acceptable salts thereof.

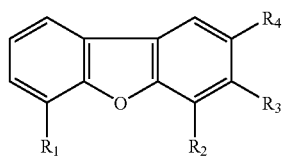

(II)

wherein $R_1$ is OH; and $R_2$, $R_3$ and $R_4$ are each independently OH, OC-lower alkyl, $NH_2$, NH-lower alkyl, SH or S-lower alkyl;

and pharmaceutically or cosmetically acceptable salts thereof.

The invention unexpectedly found that the compounds of Formula (I) having two hydroxyl groups at 3 and 5 positions of biphenyl had advantageous tyrosinase inhibitory activity and that the compounds of Formula II had tyrosinase inhibitory activity.

In the context of the present specification, the term "lower alkyl" refers to a monoradical branched or unbranched saturated hydrocarbon chain of 1 to 10 atoms. Preferably, the carbon number of alkyl is selected from the group consisting of 1 to 8; more preferably, it is $C_{1-6}$ alkyl or $C_{1-4}$ alkyl. Examples of alkyl groups include methyl (—$CH_3$), ethyl (—$CH_2CH_3$), propyl (—$CH_2CH_2CH_3$), isopropyl($CH_3$)$_2$CH and butyl (—$C_4H_9$).

According to one embodiment of the compounds of Formula (I) of the invention, $X_1$, $X_2$ and $X_3$ are preferably OH or $OC_{1-6}$alkyl and $X_4$ is glucopyranose. More preferably, $X_1$ is $OCH_3$; $X_2$ is OH, $X_3$ is OH and $X_4$ is glucopyranose.

According to one embodiment of the compounds of Formula (II) of the invention, $R_1$, $R_2$, $R_3$ and $R_4$ are each independently OH or $OCH_3$. Preferably, $R_1$ is OH, $R_2$ is $OCH_3$, $R_3$ is OH and $R_4$ is $OCH_3$.

In the context of the present specification, the term "pharmaceutically or cosmetically acceptable salt" includes those formed with both organic and inorganic acids and bases. Pharmaceutically or cosmetically acceptable acid addition salts include those formed from mineral acids such as: hydrochloric, hydrobromic, sulphuric, and phosphoric acid; and organic acids such as: citric, tartaric, lactic, pyruvic, acetic, trifluoroacetic, succinic, oxalic, formic, fumaric, maleic, oxaloacetic, methanesulphonic, ethanesulphonic, p-toluenesulphonic, benzenesulphonic and isethionic acids. Pharmaceutically acceptable base salts include ammonium salts, alkali metal salts such as those of sodium and potassium, alkaline earth metal salts such as those of calcium and magnesium and salts with organic bases, including salts of primary, secondary and tertiary amines.

According to one embodiment of the compounds of formula (II) of the invention, $R_2$ and $R_4$ are preferably each independently OH or $OC_{1-6}$alkyl. More preferably, $R_2$ and $R_4$ are each independently OH or $OCH_3$.

According to the invention, the compounds of formulae (I) and (II) can be prepared by a synthesis procedure known in the art. The synthesis of the compounds of formula (I) is shown below in scheme 1:

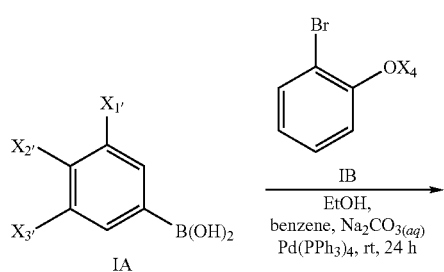

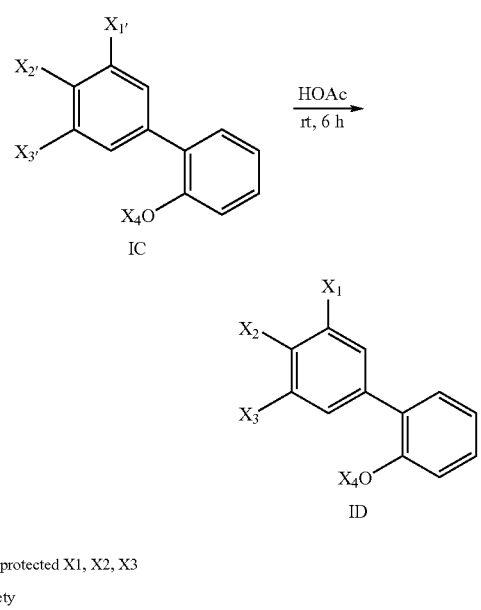

$X_1'$, $X_2'$, $X_3'$ trifluoroacetyl protected X1, X2, X3

X4: sugar moiety

Referring to Reaction Scheme 1, to a solution of a compound of Formula IA wherein $X_1'$, $X_2'$ and $X_3'$ are protecting group (such as trifluoroacetyl protecting group), in a mixture of a nonpolar, aprotic solvent (such as benzene) and a polar, protic solvent (such as ethanol) a compound IB is added wherein $X_4$ is a sugar moiety. The resulting mixture reacts in the presence of a catalyst (such as Pd(PPh$_3$)$_4$) at room temperature for 24 hours to obtain a compound IC. The compound IC reacts with HOAc at room temperature for 6 hours so that the protecting groups can be removed to obtain a compound of Formula (I).

The synthesis of the compounds of formula (II) is shown below in scheme 2:

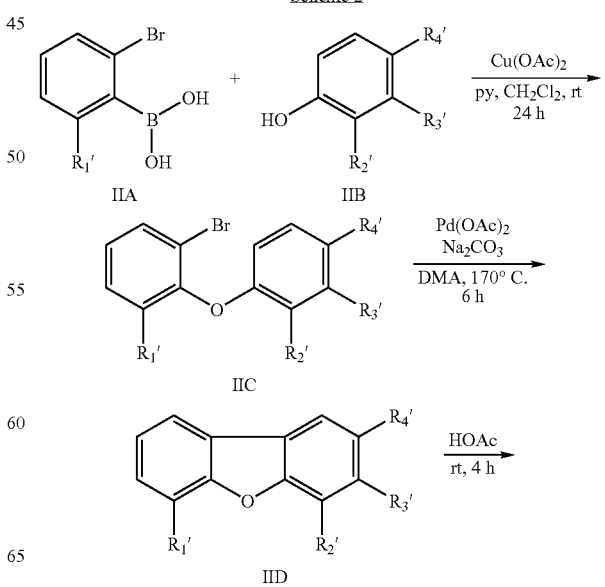

-continued

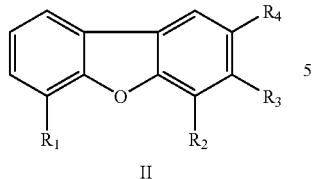

II

R$_1$, R$_2$, R$_3$, R$_4$'
trifluoroacetyl protected R$_1$, R$_2$, R$_3$, R$_4$ Referring to Reaction Scheme 2, a compound of Formula IIA reacts with a compound of Formula IIB in a nonpolar, aportic solvent (such as CH$_2$Cl$_2$) in the presence of Cu(OAc)$_2$ at room temperature for 24 hours to obtain a compound of Formula IIC. The compound of Formula IIC wherein R$_1$', R$_2$', R$_3$' and R$_4$' are a protecting group (such as trifluoroacetyl protecting group) is reacted in a polar, aprotic solvent such as dimethylamine (DMA) in the presence of a catalyst (such as Pd(OAc)$_2$) to obtain a compound of Formula IID. The compound IID reacts with HOAc at room temperature for 4 hours so that the protecting groups can be removed to obtain a compound of Formula (II).

The *Pyracantha koidzumii* extract and the compounds of formulae (I), (II) and their pharmaceutically or cosmetically acceptable salts may be used on their own but will generally be administered in the form of a pharmaceutical or cosmetic composition in which the *Pyracantha koidzumii* extract or the formula (I) compound/formula (II) compound/salt is in association with a pharmaceutically or cosmetically acceptable adjuvant, diluent or carrier.

The pharmaceutical compositions may be administered systemically, e.g., by oral administration in the form of tablets, capsules, syrups, powders or granules; or by parenteral administration in the form of solutions or suspensions; or by subcutaneous administration; or by topical administration; or transdermally.

Excess melanin production or abnormal distribution can cause irregular hyperpigmentation of the skin. In order to develop therapies or prophylactics that improve or prevent hyperpigmentary disorders, such as melasma, and age spots, disruption of tyrosinase activity has usually been targeted (Journal of Investigative Dermatology (2007), 127: 751-61). The *Pyracantha koidzumii* extract and the compounds of the invention have tyrosinase inhibitory activity, so they can be used as skin whitening agents and in the prevention and therapy of symptoms resulting from undesirable effects of tyrosinase activity, for example, age spots, melanoma, erythema, sunburn, melasma, ephelides, and pigmented cosmetic dermatitis.

EXAMPLE

Example 1

Extraction of *Pyracantha Koidzumii*

Plants of *Pyracantha koidzumii* were pressed and then extracted with 40 ml of 95% ethanol three times. The resulting ethanol solutions were combined (total 120 ml) and concentrated under reduced pressure to obtain 360 g of 95% ethanol raw extract. The raw extract was suspended in water and then extracted with ethyl acetate (EtOAc) to obtain an ethyl acetate extract of *Pyracantha koidzumii*.

Example 2

Fraction of EtOAc Extract and Isolation of the Compounds of the Invention

The EtOAc extract of Example 1 was dissolved in water and isolated with Diaion HP 20 column by a gradient elution of 100% water to 100% ethanol. The resulting elutes were assayed by Thin Layer Chromatography (TLC) plate (CH$_2$Cl$_2$/Methanol/Acetic acid=7:1:0.1) and seven fractions (PK-1-1 to PK-1-7) were obtained. The fractions, PK-1-3 (1.99 g), PK-1-4 (1.15 g) and PK-1-5 (15.42 g), were further isolated with C$_{18}$ column by a gradient elution of 100% water to 100% methanol and the following fractions were obtained: PK-1-3-1 to PK 1-3-8, PK-1-4-1 to PK-1-4-8 and PK-1-5-1 to PK-1-5-10. These fractions were further isolated by different columns. Two new compounds were found, one in fraction PK 1-3-5 and the other in PK-1-5-4. PK-1-3-5 was isolated by Reverse phase high performance liquid chromatography (RP-HPLC) (column: Biosil 5 ODS-W 10 mm×I.D. 250 mm; mobile phase: 22% methanol; flow rate: 3 ml/min; detector: UV 280 nm). A new compound MHL-1, 3,4-dihydroxy-5-methoxybiphenyl-2'-O-β-d-glucopyranoside, appeared at the retention time of 38 minutes. The identification data of this compound are as follows:

Amorphous Brown Powder
$[\alpha]_D^{24.5}$ –10.6° (c 0.5, MeOH)
UV (MeOH) $\lambda_{max}$(log ε): 265 (3.74) nm
ESI-MS (negative) m/z 393.1 [M–H]$^-$
HRESIMS m/z 393.1202[M–H]$^-$ (calculated for 394.1264)
$^1$H-NMR (500 MHz, CD$_3$OD) δ$_H$ 6.67 (1H, d, J=1.8, H-2), 6.80 (1H, d, J=1.8 Hz, H-6), 7.22 (1H, m, H-3'), 7.23 (1H, dd, =8.5, 1.4 Hz, H-4'), 7.02 (1H, m, H-5'), 7.27 (1H, dd, J=8.5, 1.4 Hz, H-6'), 5.03 (1H, d, J=7.2, H-1''), 3.43 (1H, m, H-2''), 3.42 (1H, m, H-3''), 3.34 (1H, m, H-4''), 3.44 (1H, m, H-5''), 3.68 (1H, dd, J=5.4, 12.0, H-6''), 3.86 (1H, dd, J=2.1, 12.0, H-6''), 3.86 (3H, s, 3'OCH$_3$)
$^{13}$C-NMR (125 MHz, CD$_3$OD) δ$_C$ 130.6 (C-1), 111.4 (C-2), 146.0 (C-3), 134.6 (C-4), 149.1 (C-5), 106.8 (C-6), 133.0 (C-1'), 155.4 (C-2'), 116.4 (C-3'), 129.0 (C-4'), 123.4 (C-5'), 131.7 (C-6'), 101.8 (C1'), 75.0 (C2'), 78.2 (C3'), 71.3 (C4'), 78.3 (C5'), 62.5 (C6'), 56.8 (3'-OCH$_3$)

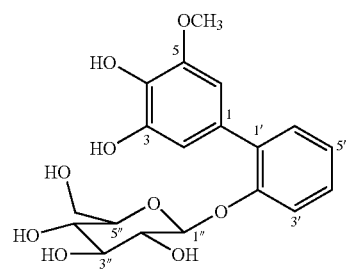

PK 1-5-4 was further isolated with C$_{18}$ column by a gradient elution of 100% water to 100% methanol and eight fractions, PK 1-5-4-1 to PK 1-5-4-8, were obtained. PK 1-5-4-2 was further eluted with C$_{18}$ column by a gradient elution of 100% water to 100% methanol and seven fractions, PK 1-5-4-2-1 to PK 1-5-4-2-7, were obtained. PK 1-5-4-1-1, was isolated by RP-HPLC (column: Biosil 5 ODS-W 10 mm×I.D.

250 mm; mobile phase: 55% methanol; flow rate: 3 ml/min; detector: RI). A new compound MHL-2, 3,6-dihydroxy-2,4-dimethoxy-dibenzofuran, appeared at the retention time of 12 minutes. The identification data of this compound are as follows:

Amorphous Brown Powder

UV (MeOH) $\lambda_{max}$(log ε): 316 (3.78), 290 (3.91), 263 (3.91) nm

ESI-MS (positive) m/z 261.5 [M+H]$^+$

HREIMS m/z 260.0687 (calculated for 260.0679)

$^1$H-NMR (500 MHz, CD$_3$OD) $\delta_H$ 7.21 (1H, s, H-1), 6.82 (1H, m, H-7), 7.08 (1H, m, H-8), 7.33 (1H, m, H-9), 3.91 (3H, s, 2-OCH$_3$), 4.11 (3H, s, 4-OCH$_3$)

$^{13}$C-NMR (125 MHz, CD$_3$OD) $\delta_C$ 98.3 (C-1), 147.4 (C-2), 140.0 (C-3), 134.7 (C-4), 144.6 (C-4a), 146.0 (C-5a), 144.1 (C-6), 113.5 (C-7), 111.5 (C-8), 124.5 (C-9), 127.9 (C-9a), 117.4 (C-9b), 57.3 (2-OCH$_3$), 61.3 (4-OCH$_3$)

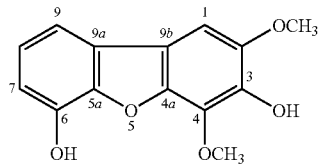

Example 3

Assay of Tyrosinase Activity in Human Melanocyte Cells

Human melanocyte (HEMn) cells are cultured with medium 254 containing antibiotics and growth factors (Cascade Biologics, Inc., Portland, Oreg., USA) in an incubator with 5% CO$_2$ for serial passage. Passages 3 to 10 of the HEMn cells were used in the experiments below.

HEMn cells were further cultured for 48 hours and then the ethyl acetate extract of the invention and the test compounds (MHL-1: 3,4-dihydroxy-5-methoxybiphenyl-2'-O-β-d-glucopyranoside and MHL-2: 3,6-dihydroxy-2,4-dimethoxy-dibenzofuran) were added. After 24 hours, the cells were washed with PBS buffer. Lysis buffer (1% Triton X-100, 1 mM phenylmethylsulfonyl fluoride (PMSF), 1 µg/ml aprotinin, and 10 µg/ml leupeptin) was added to the resulting cells to obtain the cell proteins. The cell proteins were kept at −80° C. Subsequently, the cell proteins were thawed and then centrifuged at 12,000 rpm for 5 minutes. The supernatant was taken for determination of the amount of protein by BCA protein assay. The proteins with different concentrations were added to a 96-well microplate and then PBS buffers were added. L-DOPA was added to the microplate to react with the protein at 37° C. for 1 hour. The absorbance of the solution at 475 nm wavelength was detected. Tyrosinase activity (%)= (OD$_{475}$ of the sample/OD$_{475}$ of control)×100.

Figure 2:
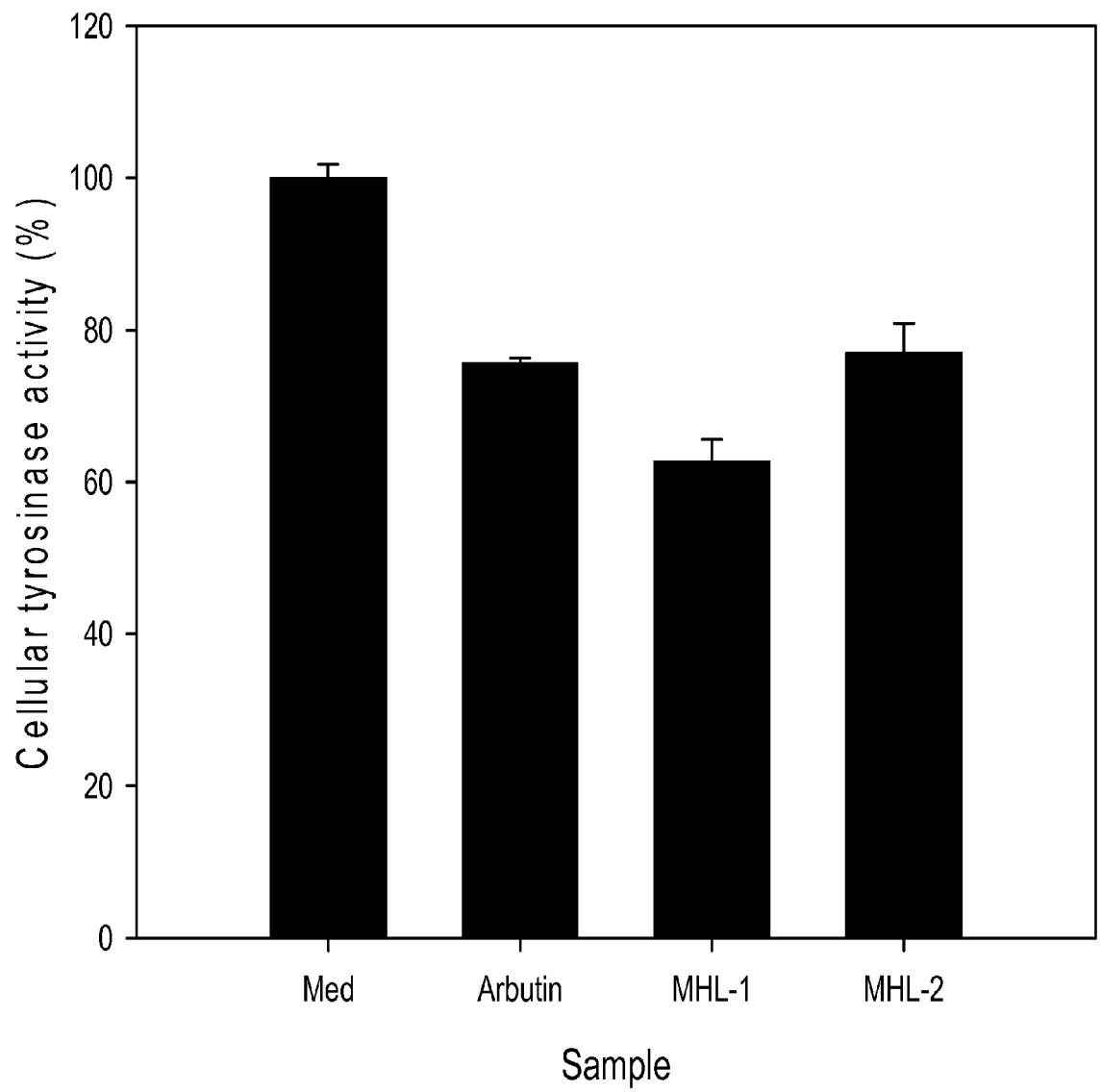
FIG. 2 shows the expression of cellular tyrosinase inhibitory activities of the compounds, MHL-1 and MHL-2, of the invention in HEMn.

Arbutin as positive control and 1% DMSO as blank were used in the tyrosinase activity assay stated above. FIG. 1 shows that the ethyl acetate extract of the invention has more than 40% inhibitory activity on tyrosinase. FIG. 2 shows that the compound of the invention, MHL-2, has tyrosinase inhibitory activity similar to that of arbutin but MHL-1 has superior activity compared to arbutin. MHL-1 and MHL-2 inhibit around 40% and 20% tyrosinase activity, respectively. The ethyl acetate extract and the compounds of the invention are effective in inhibiting tyrosinase.

Example 4

Tyrosinase Oxidative Activity Analysis by L-Dopa Staining of SDS-PAGE Gels

Figure 3:
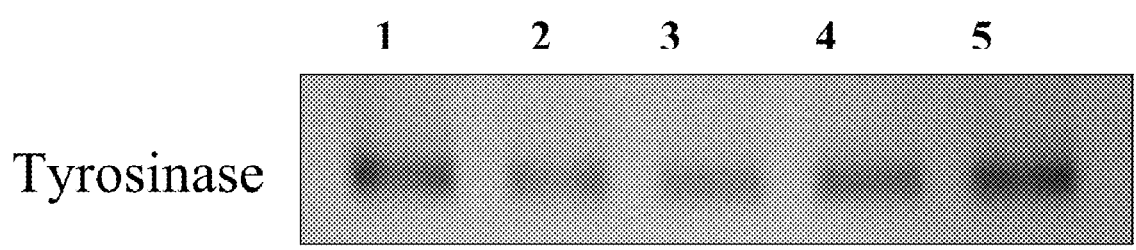
FIG. 3 shows the L-dopa staining of electrophoresed gels of tyrosinase. Lane 1: medium only; Lane 2: arbutin 2.5 mM; Lane 3-5: 100, 80 and 60 μM of MHL-1.
Figure 4:
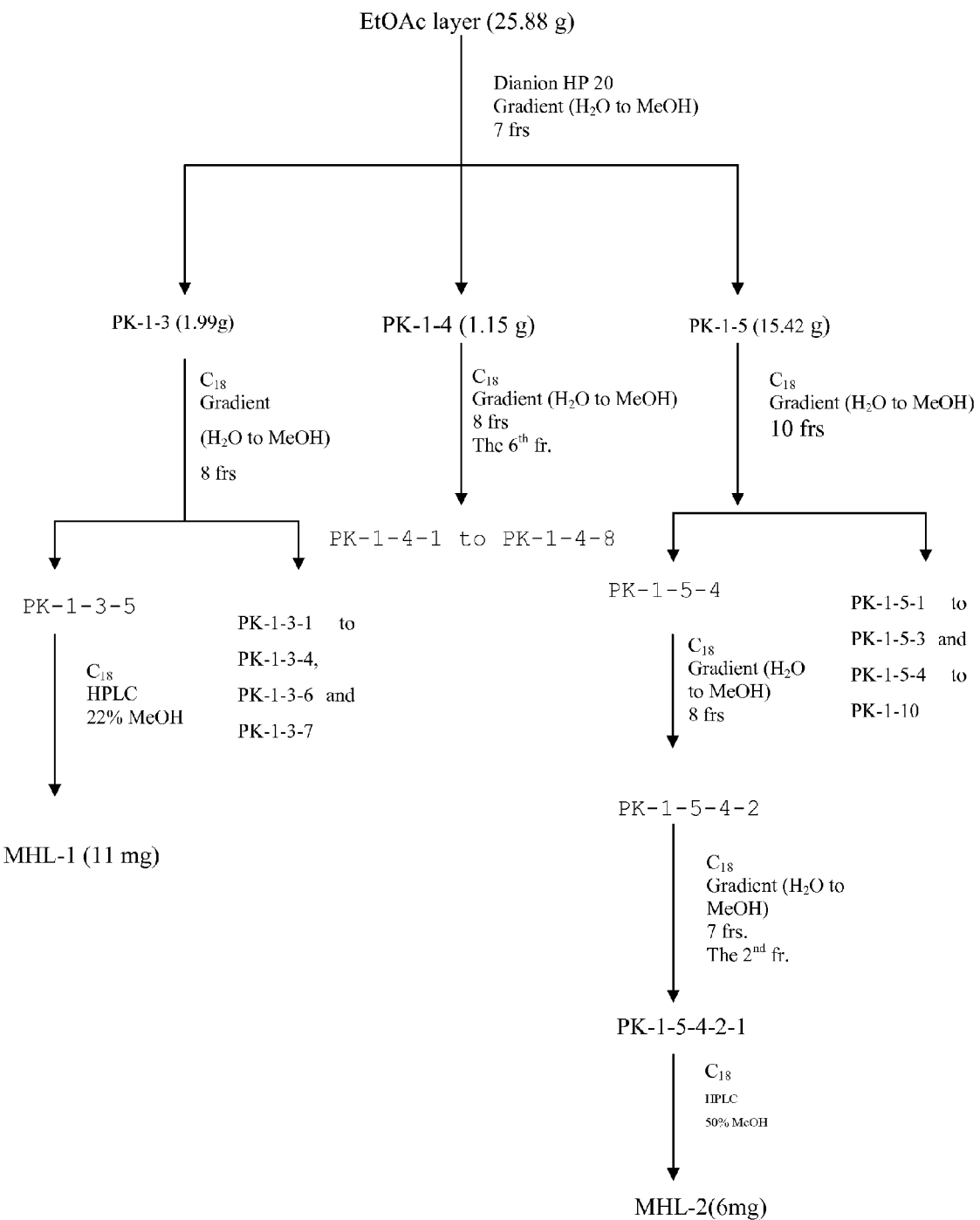
FIG. 4 shows a flow chart summarizing the isolation of the ethyl acetate extract.

The compound of the invention, MHL-1, with different concentrations was added to HEMn cells. The lysis of HEMn cells, isolation of cell proteins and BCA protein assay were performed on the supernatant obtained as stated in Example 1 so that the amount of the protein could be determined. 10% SDS-polyacrylamide gel electrophoresis (dd-H2O; 10% Acrylamide mix; 1.5M Tris-base pH8.8; 10% SDS; 10% Ammonium persulfate; TEMED) was performed on the resulting protein and the sample buffer (60 mM Tris-HCl, pH 6.8, 2% sodium dodecyl sulfate (SDS), 10% glycerol, 0.01% bromophenol blue) at the same time. The molecular weight of tyrosinase was about 72 kDa. The resulting gels were washed with 0.1 M of PBS (pH 6.8) for 30 minutes and then the protein at the position of 72 kDa reacted with 5 mM L-DOPA in 0.1 M PBS at 37° C. for 1 hour. After the reaction, Quantity One 1-D software was used to determine the amount of protein. As shown by FIG. 3, the higher the concentration of MHL-1, the lower the tyrosinase oxidative activity.

What is claimed is:

1. A *Pyracantha koidzumii* extract, which is produced by the following steps: extracting *Pyracantha koidzumii* with ethanol to obtain an ethanol extract and extracting the ethanol extract with ethyl acetate to obtain ethyl acetate extract.

2. The extract of claim 1, which further comprises the step of fractioning the ethyl acetate extract by liquid phase chromatography with solvent elution.

3. The extract of claim 1, which further comprises the step of fractioning the ethyl acetate extract by HPLC with C$_8$ to C$_{18}$ column by a gradient elution of water to methanol.

4. The exact of claim 3, wherein the resulting fraction is further fractioned by HPLC with a gradient elution of methanol.

5. The extract of claim 4, wherein 10% to 100% methanol is used in the gradient elution of methanol.

6. The extract of claim 5, wherein 20% to 50% methanol is used in the gradient elution of methanol.

7. The extract of claim 5, wherein about 20%, 22% or 50% is used in the gradient elution of methanol.

8. A pharmaceutical or cosmetic composition, which comprises the extract of claim 1 or the fraction of claim 4 or 7.

9. A method of preparing a *Pyracantha koidzumii* extract comprises the following steps: extracting *Pyracantha koidzumii* with ethanol to obtain an ethanol extract and extracting the ethanol extract with ethyl acetate to obtain the said *Pyracantha koidzumii* extract.

10. The method of claim 9, which further comprises the step of fractioning the ethyl acetate extract by liquid phase chromatography with solvent elution.

11. The method of claim 9, which further comprises the step of fractioning the ethyl acetate extract by HPLC with C$_8$ to C$_{18}$ column by a gradient elution of water to methanol.

12. The method of claim 11, wherein the resulting fraction is further fractioned by HPLC with a gradient elution of methanol.

13. The method of claim 12, wherein 10% to 100% methanol is used in the gradient elution of methanol.

14. The method of claim 13, wherein 20% to 50% methanol is used in the gradient elution of methanol.

15. The method of claim 13, wherein about 20%, 22% or 50% is used in the gradient elution of methanol.

* * * * *